United States Patent [19]

Ogata et al.

[11] Patent Number: 4,988,709
[45] Date of Patent: Jan. 29, 1991

[54] QUINOLONE-CARBOXYLIC ACIDS AS ANTIBACTERIAL AGENTS

[75] Inventors: Masaru Ogata, Hyogo; Hiroshi Matsumoto, Osaka; Sumio Shimizu, Hyogo; Shiro Kida, Osaka, all of Japan

[73] Assignee: Shionogi & Co., Ltd., Osaka, Japan

[21] Appl. No.: 353,321

[22] Filed: May 15, 1989

[30] Foreign Application Priority Data

May 23, 1988 [JP] Japan ............... 63-126695

[51] Int. Cl.$^5$ ............... C07D 215/16; C07D 215/54; A61K 31/47
[52] U.S. Cl. .................. 514/314; 514/312; 514/230.2; 514/300; 546/156; 546/123
[58] Field of Search ................ 546/156; 514/312, 314

[56] References Cited

U.S. PATENT DOCUMENTS 4,382,892 5/1983 Hayakawa et al. ............... 540/575
4,528,287 7/1985 Itoh et al. ............... 514/254

FOREIGN PATENT DOCUMENTS 0047005 3/1982 European Pat. Off. ............ 514/254
0106489 4/1984 European Pat. Off. ............ 546/123
0159174 10/1985 European Pat. Off. ............ 544/101
0172651 2/1986 European Pat. Off. ............ 544/101
2158825 11/1985 United Kingdom ............ 546/123

Primary Examiner—Alan L. Rotman
Attorney, Agent, or Firm—Wenderoth, Lind & Ponack

[57] ABSTRACT

Novel pyridonecarboxylic acids of the formula:

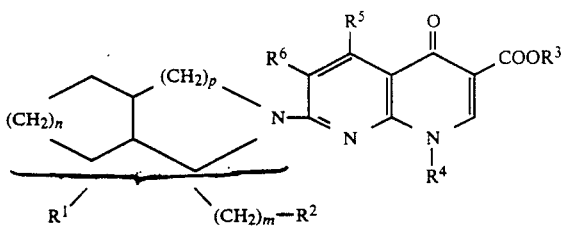

or

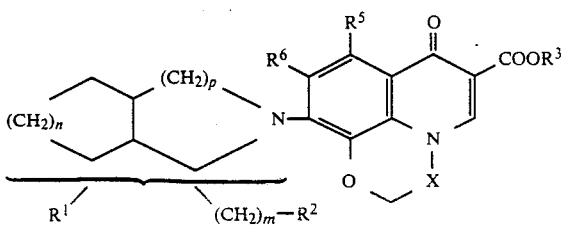

or the pharmaceutically acceptable salts thereof having a more potent and longer lasting antibacterial activities against gram-positive and gram-negative bacteria than known analogues, useful for antibacterial agents at an oral dose of 1-500 mg, preferably 50-100 mg per day to an adult.

39 Claims, No Drawings

QUINOLONE-CARBOXYLIC ACIDS AS ANTIBACTERIAL AGENTS

BACKGROUND OF THE INVENTION

1. Field of the Invention

The present invention relates to novel pyridonecarboxylic acids exhibiting excellent antibacterial activities against gram-positive and gram-negative bacteria.

2. Prior Art

The compounds described in U.S. Pat. No. 4,382,892, FR. Pat. No. 2,563,521 and U.S. Pat. No. 4,528,287 Specifications have been known as pyridonecarboxylic acid antibacterial agents. Many of these conventional products have problems such as induction of adverse effect like convulsions when administered to humans. Consequently, the aim of this invention is to supply antibacterial agents having strong antibacterial activity together with reduced CNS adverse reactions such as convulsion.

SUMMARY OF THE INVENTION

This invention relates to pyridonecarboxylic acid compounds possessing an azabicyclo ring at the 7-position. The compounds of the present invention are particularly valuable for antibacterial agents by oral administration.

DETAILED DESCRIPTION

The present invention relates to compounds of the formula:

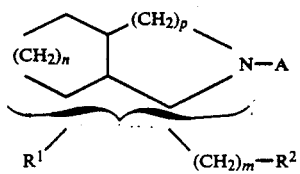

(I)

wherein $R^1$ is hydrogen, hydroxy, $C_1$-$C_4$ alkyl, $C_1$-$C_4$ alkoxy, oxo, halogen, or amino optionally substituted by a member selected from the group consisting of $C_1$-$C_4$ alkyl and $C_1$-$C_4$ alkanoyl; $R^2$ is azido, hydroxy, $C_1$-$C_4$ alkoxy, $C_1$-$C_4$ alkoxycarbonyl, $C_1$-$C_4$ alkanoyl, or amino optionally substituted by a member selected from the group consisting of $C_1$-$C_4$ alkyl and $C_1$-$C_4$ alkanoyl; A is

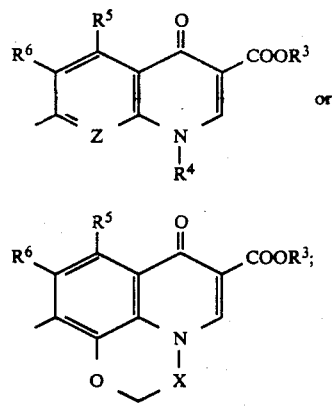

$R^3$ is hydrogen or carboxy-protecting group; $R^4$ is $C_1$-$C_4$ alkyl, $C_2$-$C_5$ alkenyl, $C_3$-$C_5$ cycloalkyl, mono- or di-fluorophenyl, or 5- or 6-membered heterocyclic group optionally substituted by a member selected from the group consisting of halogen and $C_1$-$C_4$ alkyl; $R^5$ is hydrogen, amino, hydroxy, or $C_1$-$C_4$ alkoxy; $R^6$ is halogen; X is CH—($C_1$-$C_4$alkyl), C=$CH_2$, N—H, or N—($C_1$-$C_4$alkyl); Z is CQ or N; Q is hydrogen, $C_1$-$C_4$ alkoxy, halogen, $C_1$-$C_4$ alkyl, or cyano; m is an integer of 0 or 1; n and p each is an integer of 1 to 3, or pharmaceutically acceptable salts thereof.

In the specification, $C_1$-$C_4$ alkyl means straight or branched chain $C_1$-$C_4$ alkyl, including methyl, ethyl, n-propyl, isopropyl, n-butyl, sec-butyl, isobutyl, tert-butyl, and the like.

Halogen means chlorine, bromine, or fluorine.

Carboxy-protecting group means $C_1$-$C_4$ alkyl.

5- or 6-membered heterocyclic group means thienyl, furyl, pyranyl, pyrolyl, imidazolyl, thiazolyl, and pyrazinyl, etc.

The compound (I) of this invention can be prepared by reacting a compound of the formula:

Hal-A(II)

wherein Hal is halogen and A has the same meaning as defined above, with a compound of the formula:

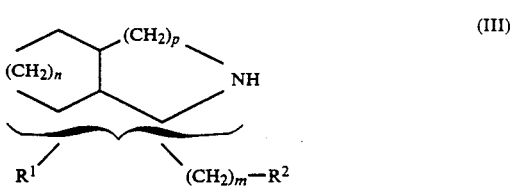

(III)

wherein $R^1$, $R^2$, m, n, and p have the same meanings as defined above.

When the substituted amino is contained in $R^1$ and/or $R^2$, it may be further subjected to deprotective reaction, if desired, and led to a compound (Ia) in which the substituent has been eliminated from the substituted amino in $R^1$ and/or $R^2$.

Thus, the method for manufacturing the compound (I) is shown by the following scheme:

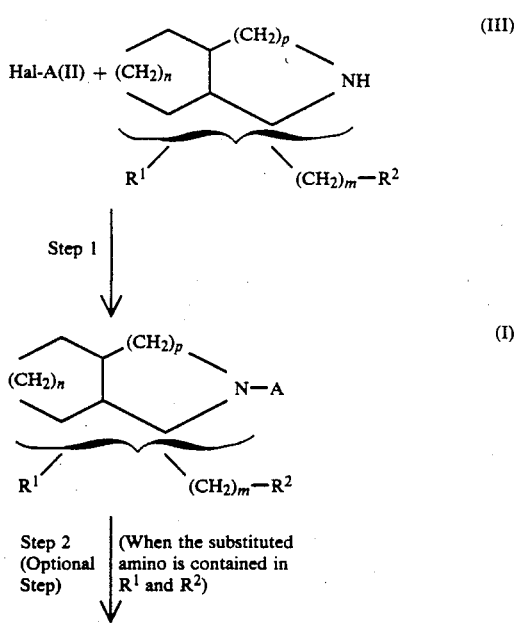

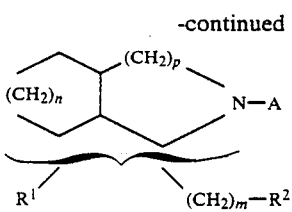

(Compound in which the substituent has been eliminated from the substituted amino in $R^1$ and/or $R^2$)

wherein A, $R^1$, $R^2$, m, n, and p have the same meanings as defined above.

The following will be explanations about the respective steps:

STEP 1

The compound (I) of this invention can be prepared by reacting the starting material (II) with the amine (III). This reaction can be performed in a solvent such as water, an alcohol, acetonitrile, dimethyl sulfoxide (DMSO) or dimethylformamide (DMF). The reaction is performed at 15°-200° C., preferably at 80°-120° C. or around the boiling point of the solvent for one to several hours. According to a conventional manner, bases such as triethylamine, pyridine, or DBU may be added in order to accelerate the reaction.

STEP 2

When the substituted amino is contained in $R^1$ or $R^2$ of the formula (I), I may be subjected, if desired, to deprotective reaction and led to (Ia). In other words, the deprotective reaction can be easily performed in a conventional manner using bases such as sodium hydroxide or potassium hydroxide and acids such as hydrochloric acid or acetic acid in a solvent such as water, aqueous alcohol, or aqueous acetic acid, at a temperature from room temperature to around the boiling point of the solvent. The starting material of the formula (II) can be synthesized by the method described in U.S. Pat. No. 4,382,892 Specification.

The compound represented by the formula (I) can be converted to acid-addition salt thereof in a conventional manner, if desired. The salt-forming acid illustratively includes an inorganic acid such as hydrochloric acid, sulfuric acid or, phosphoric acid and an organic acid such as methanesulfonic acid, lactic acid, oxalic acid, or acetic acid.

The compound may also be led to a salt of alkaline metal such as sodium or potassium.

The compound (I) of this invention can be administered orally or parenterally to humans or mammals. They can be formulated into tablets, capsules, pills, granules, injections, suppositories, and syrups by conventional pharmaceutical practice. The pharmaceutically acceptable carriers, diluents, and fillers include lactose, cane sugar, wheat starch, potato starch, magnesium stearate, gelatin, methyl cellulose, agar, water, etc. Stabilizers, emulsifiers, wet extenders, buffers, and other auxiliaries may be added appropriately, if necessary. Suitable daily doses are 1-500 mg for oral administration and 0.1-300 mg for injection.

The following examples, reference examples and formulation are shown to clarify the practical embodiment of this invention.

The abbreviations used in the examples, reference examples and tables shall have the following meanings:
Et: Ethyl
Me: Methyl
Ac: Acetyl
DBU: 1,8-Diazabicyclo[5,4,0]undecen-1

EXAMPLE 1

1-Cyclopropyl-7-[(1R*,5S*,6S*)-6-aminomethyl-3-azabicyclo[3,3,0]octane-3-yl]-6,8-difluoro-1,4-dihydro-4-oxo-3-quinolinecarboxylic acid (I-1)

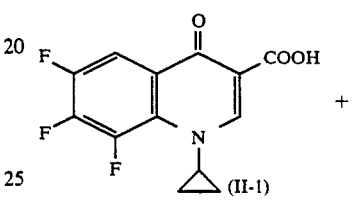

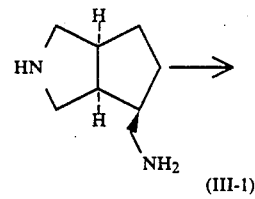

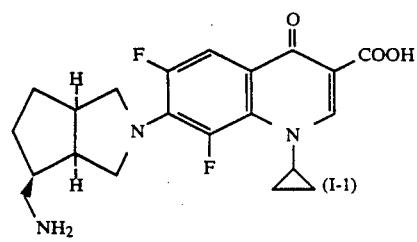

To a suspension of 200 mg of 1-cyclopropyl-6,7,8-trifluoro-1,4-dihydro-4-oxo-3-quinolinecarboxylic acid (II-1) and 149 mg of (1R*,5S*, 6S*)-6-aminomethyl-3-azabicyclo[3,3,0]octane (III-1) in 12 ml of acetonitrile is added a solution of 161 mg of DBU in acetonitrile under stirring, and the mixture is heated and refluxed under nitrogen atmosphere for 2 hours. After cooling, the resulting crystals are collected by filtration and recrystallized from methanol-chloroform to give 108 mg (yield: 38%) of the objective compound (I-1).
m.p. 235°-242° C.

Anal Calcd. (%) for $C_{21}H_{23}F_2N_3O_3$: C, 62.21; H, 5.72; F, 9.37; N, 10.36, Found (%): C, 62.43; H, 5.83, F, 9.20; N, 10.28.

EXAMPLES 2-20

The reaction is performed as described in Example 1, whereby the objective compound (I) are obtained.

The physical properties of the objective compounds are shown in Tables 1 and 2.

TABLE 1

$$\text{(I)}$$

Structure (I): A fused ring system with R⁵, R⁶ substituents, a carbonyl, COOR³ group, Z linker, N-R⁴, and an amine substituent bearing (CH₂)ₙ, (CH₂)ₚ, R¹, and (CH₂)ₘ-R² groups.

| Compound No. | R¹ / (CH₂)ₘ–R² (ring structure) | R³ | R⁴ | R⁵ | R⁶ | Z | Melting point (°C.) | Molecular formula | Elementary Analysis (%) Found(Calcd.) | Coordination |
|---|---|---|---|---|---|---|---|---|---|---|
| I-2 | 4-NH₂, 5-OH cis-fused bicyclic pyrrolidine (positions 1,2,3,5,6,7,8) | H | Δ | H | F | C—F | 230 (dec.*) | C₂₀H₂₁F₂N₃O₄ · 1/3CHCl₃ | C,54.86(54.61) H,4.83(5.16) F,8.53(8.33) N,9.44(9.67) | 1R*,5S*, 6R* |
| I-3 | NH₂, OH cis-fused bicyclic pyrrolidine | H | Δ | H | F | C—F | 275 (dec.) | C₂₀H₂₁F₂N₃O₄ · 1/2CHCl₃·3/2H₂O | C,50.33(49.97) H,5.02(4.95) F,7.72(7.67) N,8.54(8.49) | 1R*,5R*, 6S* |
| I-4 | H₂N-substituted octahydroisoindole (positions 1–9) | H | Δ | NH₂ | F | C—F | 241–242 (dec.) | C₂₁H₂₄F₂N₄O₃·2HCl | C,51.33(51.03) H,5.33(5.92) F,7.73(7.44) N,11.40(11.47) | 1R*,2R*, 6S* |
| I-5 | Decahydroisoquinoline with NH₂ at position 7 | H | Δ | H | F | C—F | 215–217 (dec.) | C₂₂H₂₆F₂N₃O₃·2.7H₂O | C,56.48(56.69) H,6.82(6.57) F,8.26(8.15) N,9.21(9.02) | 1R*,6R*, 7S* |
| I-6 | Octahydrocyclohepta[b]pyrrole with NH₂ | H | Δ | H | F | N | 277–279 (dec.) | C₂₁H₂₆FN₄O₃ | C,60.11(60.27) H,6.28(6.50) F,4.91(4.54) N,13.33(13.39) | 1R*,2S*, 7S* |
| I-7 | NH₂-substituted octahydroisoindole | H | Δ | NH₂ | F | C—F | 227–229 (dec.) | C₂₁H₂₄F₂N₄O₃·HCl·1.2H₂O | C,52.58(52.93) H,5.87(5.80) Cl,7.94(7.44) F,7.84(7.97) N,11.78(11.76) | 1R*,2S*, 6S* |
| I-8 | MeNH-substituted bicyclic pyrrolidine | H | Δ | NH₃ | F | C—F | 251 (dec.) | C₂₅H₃₄F₃N₄O₃·HCl·H₃O | C,54.12(54.26) H,5.98(6.00) Cl,7.50(7.28) F,7.43(7.80) N,11.31(11.51) | 1R*,5S* |

TABLE 1-continued (I)

| Compound No. | R¹ / (CH₂)ₘ—R² | R³ | R⁴ | R⁵ | R⁶ / Z | Melting point (°C.) | Molecular formula | Elementary Analysis (%) Found(Calcd.) | Coordination |
|---|---|---|---|---|---|---|---|---|---|
| I-9 | NH₂ (bicyclic) | H | Δ | NH₂ | F  C—F | 243 (dec.) | $C_{20}H_{23}F_2N_4O_3 \cdot HCl \cdot 1.5H_2O$ | C,50.94(51.34) H,5.52(5.60) Cl,7.50(7.58) F,7.77(8.12) N,11.82(11.97) | 1R*,5S*, 6S* |
| I-10 | (bicyclic with NH₂) | H | Δ | H | F  C—F | 132 | $C_{22}H_{26}F_2N_3O_3 \cdot 2.1H_2O$ | C,57.84(58.04) H,6.47(6.46) F,7.95(8.35) N,9.20(9.23) | 1R*,6R*, 10R* |
| I-11 | H₂N (bicyclic) | H | Δ | H | F  C—F | >258 (dec.) | $C_{20}H_{21}F_2N_3O_2 \cdot HCl$ | C,56.41(56.28) H,5.21(5.19) Cl,8.32(8.16) F,8.92(8.69) N,9.87(9.71) | 1R*,5S*, 7S* |
| I-12 | MeNH (bicyclic) | H | Δ | —OH | F  C—F | 254–255 (dec.) | $C_{22}H_{26}F_2N_3O_4 \cdot HCl \cdot 2/3H_2O$ | C,55.03(54.83) H,5.96(5.72) Cl,7.29(7.36) F,7.86(7.88) N,8.38(8.72) | 1R*,5S* |
| I-13 | NH₂ (bicyclic) | H | Δ | H | F  C—F | 256 (dec.) | $C_{21}H_{23}F_2N_3O_3 \cdot H_2O \cdot 1.2HCl$ | C,54.23(54.34) H,5.73(5.47) Cl,8.88(9.17) F,8.19(8.19) N,8.97(9.05) | 1R*,6S*, 7S* |
| I-14 | H₂N (bicyclic) | H | Δ | H | F  C—F | 192–193 | $C_{21}H_{23}F_2N_3O_3 \cdot HCl \cdot 1/2CH_3CN \cdot 2/3H_2O$ | C,55.78(55.93) H,5.83(5.50) Cl,7.81(7.50) F,8.34(8.04) N,10.42(10.37) | 1R*,6R*, 9S* |
| I-15 | H₂N (bicyclic) | H | Δ | H | F  C—F | 229–231 (dec.) | $C_{21}H_{23}F_2N_2O_3 \cdot H_2O$ | C,59.53(59.85) H,6.17(5.98) F,8.85(9.02) N,9.83(9.97) | 1R*,2S*, 6S* |

TABLE 1-continued (I)

| Compound No. | R¹ | (CH₂)ₘ—R² | R³ | R⁴ | R⁵ | R⁶ | Z | Melting point (°C.) | Molecular formula | Elementary Analysis (%) Found(Calcd.) | Coordination |
|---|---|---|---|---|---|---|---|---|---|---|---|
| I-16 | H | (cycloheptane with N— and NH₂, H) | H | Δ | —NH₂ | F | C—F | 229–231 (dec.) | $C_{22}H_{26}F_2N_4O_3 \cdot HCl \cdot 6/5H_2O$ | C,53.84(53.87) H,6.03(6.04) Cl,7.63(7.23) F,7.52(7.75) N,11.12(11.42) | 1R*,2R*, 7S* |

*dec: decomposition

TABLE 2 (I)

| Compound No. | R¹ | (CH₂)ₘ—R² | R³ | R⁵ | R⁶ | X | Y | m.p.* (°C.) | Molecular formula | Elementary Analysis (%) Found(Calcd.) | Coordination |
|---|---|---|---|---|---|---|---|---|---|---|---|
| I-17 | H | (cyclohexane fused pyrrolidine with NH₂) | H | H | F | N | Me | 250 (dec.) | $C_{20}H_{23}FN_4O_4 \cdot 13/3H_2O$ | C,50.08(50.00) H,6.07(5.80) F,4.30(3.95) N,11.72(11.66) | 1R*,2R*,6S* |
| I-18 | H | (cyclohexane fused pyrrolidine with NH₂) | H | H | F | C | Me | 251–254 (dec.) | $C_{21}H_{24}FN_3O_4 \cdot 2.5H_2O$ | C,56.97(56.49) H,6.59(6.55) F,4.55(4.26) N,9.55(9.41) | 1R*,2R*,6S* |
| I-19 | H | (cyclohexane fused pyrrolidine with NH₂) | H | H | F | C | =CH₂ | >300 | $C_{21}H_{22}FN_3O_4 \cdot HCl \cdot 0.5H_2O$ | C,57.32(57.39) H,5.50(5.36) F,4.09(4.32) N,9.39(9.56) | 1R*,2R*,6S* |

TABLE 2-continued

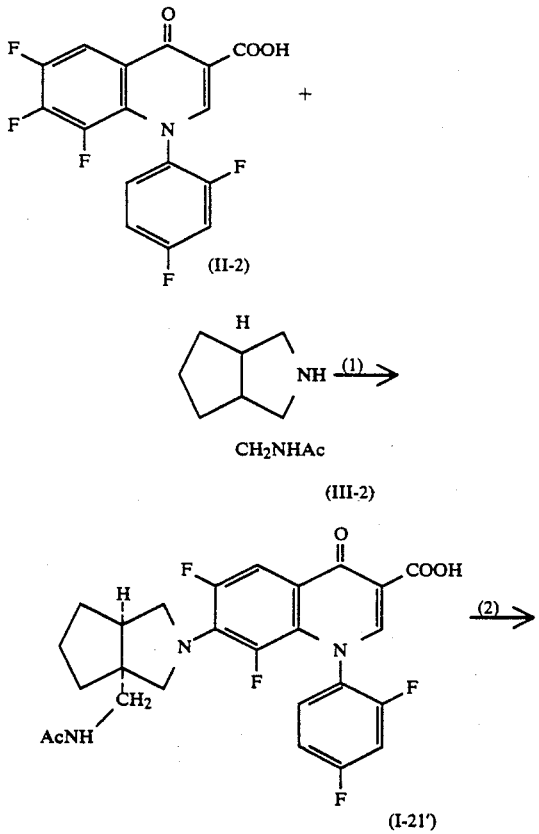

| Compound No. | R¹ / (CH₂)ₘ—R² | R³ | R⁵ | R⁶ | X | Y | m.p.* (°C.) | Molecular formula | Elementary Analysis (%) Found(Calcd.) | Coordination |
|---|---|---|---|---|---|---|---|---|---|---|
| I-20 | (structure with NH₂, cyclohexane-fused pyrrolidine) | H | H | F | N | Me | 258–260 (dec.) | $C_{20}H_{23}FN_4O_4 \cdot 1.5H_2O$ | C,55.79(55.94) H,6.16(6.10) F,4.78(4.42) N,12.92(13.05) | 1R*,2S*,6S* |

*m.p.: Melting point

EXAMPLE 21

1-(2,4-Difluorophenyl)-7-[(1R*,5S*)-1-aminomethyl-3-azabicyclo[3,3,0]octane-3-yl]-6,8-difluoro-1,4-dihydro-4-oxo-3-quinolinecarboxylic acid (I-21)

(1) To a suspension of 230 mg of (1R*, 5S*)-1-acetylaminomethyl-3-azabicyclo[3,3,0]octane hydrochloride (III-1) and 250 mg of 1-(2,4-difluorophenyl)-6,7,8-trifluoro-1,4-dihydro-4-oxo-3-quinolinecarboxylic acid (II-2) in 10 ml of acetonitrile is added 160 mg of DBU under stirring, and the solution is refluxed for 2 hours under stirring. The reaction mixture is concentrated and the residue is dissolved in methylene chloride. The organic layer is washed with water and dried over $Na_2SO_4$ and concentrated. The residue is chromatographed on a column of silica gel eluting with 7% methanol-methylene chloride. The eluate is concentrated and the residue is washed with ethyl acetate-isopropyl ether and collected by filtration to give 208 mg of light yellow crystal (I-21').

m.p. 123°–125° C.

Anal Calcd. (%) for $C_{26}H_{23}F_4N_3O_4 \cdot 0.5CH_3COOC_2H_5$: C, 59.89; H, 4.85; F, 13.53; N, 7.48, Found (%): C, 60.04; H, 4.76; F, 13.58; N, 7.80.

(2) To 8 ml of conc. hydrochloric acid is added 150 mg of the compound (I-21') and the mixture is refluxed at 130° C. for 2 hours. After the solvent is concentrated, the residue is washed with a mixture of methanol-ether, filtered and recrystallize from methanol-ethyl acetate to give 86 mg of the objective compound (I-21) as crystal.

m.p. 214°–216° C.

Anal Calcd. (%) for $C_{24}H_{21}F_4N_3O_3 \cdot HCl$: C, 56.31; H, 4.33; Cl, 6.93; F, 14.85; N, 8.21 Found (%): C, 56.16; H, 4.57; Cl, 7.15; F, 14.59; N, 8.23

EXAMPLES 22–42

The reaction is performed as described in Example 21, whereby the objective compound (I) is obtained.

The physical properties of the objective compounds are shown in Table 3 and 4.

TABLE 3

Structure (I): bicyclic amine-(CH$_2$)$_m$—R$^2$ / (CH$_2$)$_n$ / (CH$_2$)$_p$ / R$^1$ group attached via N to a quinolone core bearing R$^5$, R$^6$, Z, COOR$^3$, R$^4$, =O substituents.

| Compound | R$^1$–(bicyclic amine) | R$^3$ | R$^4$ | R$^5$ | R$^6$ | Z | m.p. (°C.) | Molecular formula | Elementary Analysis (%) Found (Calcd.) | Coordination |
|---|---|---|---|---|---|---|---|---|---|---|
| I-22 | H$_2$N– on octahydrocyclopenta[c]pyrrole (positions 4,6,7) | H | Δ | H | F | C—F | 251–253 (dec.) | $C_{20}H_{21}F_3N_2O_3 \cdot HCl \cdot 1.3H_2O$ | C, 53.47(53.51); H, 5.52(5.54); Cl, 7.89(7.54); F, 8.46(8.09); N, 9.35(9.51) | 1R*, 5S*, 6S* |
| I-23 | H$_2$N–CH$_2$– on octahydrocyclopenta[c]pyrrole | H | Δ | H | F | C—F | 235–237 (dec.) | $C_{21}H_{23}F_2N_3O_3 \cdot HCl$ | C, 50.33(49.97); H, 5.02(4.95); F, 7.72(7.67); N, 8.54(8.49) | 1R*, 5S* |
| I-24 | NH$_2$– on octahydrocyclopenta[c]pyrrole | H | Δ | H | F | C—F | 275–277 | $C_{20}H_{21}F_2N_3O_3 \cdot HCl \cdot H_2O$ | C, 54.12(54.23); H, 5.45(5.21); Cl, 7.99(8.35); F, 8.56(8.56); N, 9.47(9.60) | 1R*, 5S* |
| I-25 | MeNH– on octahydrocyclopenta[c]pyrrole | H | Δ | H | F | C—F | 106–110 | $C_{21}H_{23}F_2N_3O_3 \cdot HCl \cdot H_2O$ | C, 55.00(55.08); H, 5.62(5.72); Cl, 7.34(7.74); F, 8.45(8.30); N, 8.90(9.18) | 1R*, 5S*, 6S* |
| I-26 | H$_2$N– on octahydroisoindole (numbered 1–9) | H | Δ | H | F | C—F | 255–257 | $C_{21}H_{23}F_2N_3O_3 \cdot HCl \cdot H_2O$ | C, 54.12(54.23); H, 5.45(5.21); Cl, 7.99(8.35); F, 8.56(8.56); N, 9.47(9.60) | 1R*, 2R*, 6S* |
| I-27 | H$_2$N– on octahydrocyclopenta[c]pyrrole | H | Δ | H | F | C—F | 260 | $C_{20}H_{21}F_2N_3O_3 \cdot HCl \cdot H_2O$ | C, 54.12(53.94); H, 5.45(5.44); Cl, 7.99(7.92); F, 8.56(8.33); N, 9.47(9.17) | 1R*, 5S*, 6R* |

TABLE 3-continued (I)

| Compound | R¹ | (CH$_2$)$_m$—R² | R³ | R⁴ | R⁵ | R⁶ | Z | m.p. (°C.) | Molecular formula | Elementary Analysis (%) Found (Calcd.) | Coordination |
|---|---|---|---|---|---|---|---|---|---|---|---|
| I-28 | H$_2$N, cyclohexane-fused pyrrolidine | | H | Δ | H | F | C—Cl | 289–292 (dec.) | C$_{21}$H$_{23}$ClFN$_3$ 1/10HCl.½H$_2$O | C, 58.30(58.25) H, 6.43(6.10) Cl, 9.01(8.78) F, 4.39(4.42) N, 9.71(9.48) | 1R*, 2R*, 6S* |
| I-29 | H$_2$N, cyclohexane-fused pyrrolidine | | H | Δ | H | F | N | 290–293 (dec.) | C$_{20}$H$_{23}$FN$_4$O$_3$ .HCl.½H$_2$O | C, 55.62(55.70) H, 5.83(5.78) Cl, 8.21(8.45) F, 4.39(4.69) N, 12.97(12.85) | 1R*, 2R*, 6S* |
| I-30 | H$_2$N, cyclohexane-fused pyrrolidine | | H | Δ | H | F | C—F | 289–291 (dec.) | C$_{21}$H$_{23}$F$_2$N$_3$O$_3$ .HCl.½H$_2$O | C, 56.18(56.29) H, 5.43(5.67) Cl, 7.90(7.91) F, 8.46(8.16) N, 9.36(9.20) | 1R*, 2S*, 6S* |
| I-31 | MeNH, cyclohexane-fused pyrrolidine | | H | Δ | H | F | C—F | 276–298 (dec.) | C$_{22}$H$_{26}$F$_2$N$_3$O$_3$. HCl.½H$_2$O | C, 57.08(56.91) H, 5.88(5.93) Cl, 7.66(7.80) F, 8.20(8.03) N, 9.07(9.06) | 1R*, 2R*, 6S* |
| I-32 | H$_2$N, cycloheptane-fused pyrrolidine | | H | Δ | H | F | C—F | 265–267 (dec.) | C$_{22}$H$_{26}$F$_2$N$_3$O$_3$ .HCl.H$_2$O | C, 55.99(55.90) H, 5.98(5.72) Cl, 7.51(7.38) F, 7.04(7.49) N, 8.90(8.63) | 1R*, 2R*, 7S* |
| I-33 | H$_2$N, cyclopentane-fused pyrrolidine | | H | Δ | H | F | C—F | 276–298 (dec.) | C$_{20}$H$_{21}$F$_2$N$_3$O$_3$.HCl | C, 56.41(56.28) H, 5.21(5.19) Cl, 8.32(8.16) F, 8.92(8.69) N, 9.87(9.71) | 1R*, 5S*, 7S* |
| I-34 | MeNH, cyclopentane-fused pyrrolidine | | H | Δ | H | F | C—F | 270–271 (dec.) | C$_{22}$H$_{25}$F$_2$N$_3$O$_3$ .HCl.½H$_2$O | C, 56.81(57.08) H, 5.85(6.10) Cl, 7.85(7.66) F, 8.11(8.21) N, 8.92(9.08) | 1R*, 5S* |
| I-35 | EtNH, cyclopentane-fused pyrrolidine | | H | Δ | H | F | C—F | 261–264 (dec.) | C$_{23}$H$_{27}$F$_2$N$_3$O$_3$ .HCl.½H$_2$O | C, 53.95(54.12) H, 5.66(5.86) Cl, 13.50(13.89) F, 7.28(7.44) N, 8.02(8.23) | 1R*, 5S* |

TABLE 3-continued

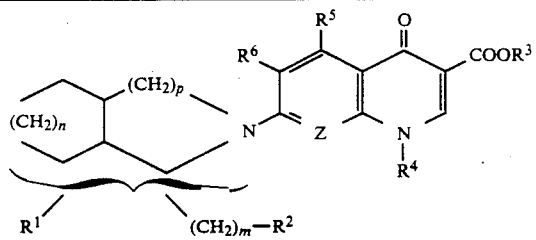

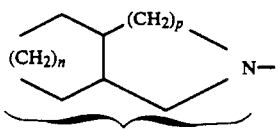

| Compound | R¹ ... (CH₂)ₘ—R² | R³ | R⁴ | R⁵ | R⁶ | Z | m.p. (°C.) | Molecular formula | Elementary Analysis (%) Found (Calcd.) | Coordination |
|---|---|---|---|---|---|---|---|---|---|---|
| I-36 | MeNH-, bicyclic (octahydroisoindole) | H | Δ | H | F | C—F | >300 | $C_{23}H_{27}F_2N_3O_3$ ·HCl·½H₂O | C, 58.23(57.92) H, 5.93(6.12) Cl, 7.50(7.43) F, 8.00(7.97) N, 8.91(8.81) | 1R*, 6S* |
| I-37 | NH₂-, bicyclopentane | H | Et | H | F | C—F | 238–240 | $C_{19}H_{21}F_2N_3O_3$ ·HCl | C, 55.44(55.14) H, 5.49(5.36) Cl, 8.45(8.57) F, 9.15(9.18) N, 10.01(10.15) | 1R*, 5S*, 6R* |
| I-38 | MeNH-, octahydropyrrolo ring | H | Δ | H | F | C—F | 282–285 | $C_{23}H_{27}F_2N_3O_3$ ·HCl·H₂O | C, 56.63(56.85) H, 6.13(6.22) Cl, 7.22(7.29) F, 7.80(7.80) N, 8.65(8.65) | 1R*, 2S*, 7S* |
| I-39 | H₂N-, octahydropyrrolo ring | H | Δ | H | F | C—F | 295–297 | $C_{22}H_{25}F_2N_3O_3$ ·HCl·½H₂O | C, 56.89(57.08) H, 5.89(6.10) Cl, 7.59(7.66) F, 7.94(8.20) N, 9.06(9.08) | 1R*, 2S*, 7S* |
| I-40 | MeNH-, octahydropyrrolo ring | H | Δ | H | F | C—F | 282–283 (dec.) | $C_{23}H_{27}F_2N_3O_3$ ·HCl·½CH₃OH | C, 57.25(57.33) H, 5.87(6.20) Cl, 7.69(7.33) F, 7.84(7.85) N, 8.62(8.68) | 1R*, 2R*, 7S* |
| I-41 | MeNH-, octahydropyrrolo ring | H | Δ | H | F | C—F | 290 (dec.) | $C_{22}H_{25}F_2N_3O_3$ ·HCl·½H₂O | C, 57.45(57.46) H, 5.84(5.72) Cl, 7.71(8.10) F, 8.26(8.24) N, 9.14(9.15) | 1R*, 2S*, 6S* |

TABLE 4

| Compound | R¹ | (CH₂)ₘ—R² | R³ | R⁵ | R⁶ | X | Y | m.p. (°C.) | Molecular formula | Elementary Analysis (%) Found (Calcd.) | Coordination |
|---|---|---|---|---|---|---|---|---|---|---|---|
| I-42 | 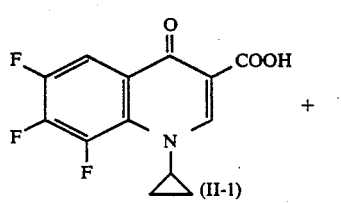 | | H | H | F | N | CH₃ | 238–240 (dec.) | C₂₁H₂₆FN₄O₄ | C, 60.81(60.57) H, 6.11(6.05) F, 4.61(4.56) N, 13.21(13.45) | 1R*, 2R*, 7S* |

EXAMPLE 43

1-Cyclopropyl-7-[(1R*,5S*)-6-oxo-3-azabicyclo[3,3,0]octane-3-yl]-6,8-difluoro-1,4-dihydro-4-oxo-3-quinolinecarboxylic acid (I-43)

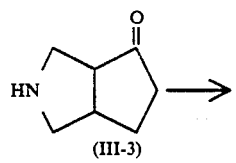

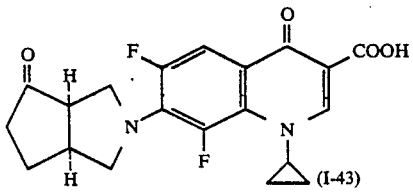

To a suspension of 200 mg of 1-cyclopropyl-6,7,8-trifluoro-1,4-dihydro-4-oxo-3-quinolinecarboxylic acid (II-1) and 350 mg of 6-oxo-3-azabicyclo[3,3,0]octane hydrochloride (II-3) in 10 ml of acetonitrile is added 330 mg of DBU under stirring and refluxed for 1 hour. The reaction mixture is concentrated and the residue is recrystallized from methanol to give 78 mg (Yield: 28%) of the objective compound (I-43). m.p. 158°–162° C. (decomposition)

Anal Calcd. (%) for C₂₀H₁₈F₂N₂O₄: C, 61.85; H, 4.67; F, 9.78; N, 7.21, Found (%): C, 61.65; H, 4.56; F, 9.54; N, 7.25.

EXAMPLE 44

1-Cyclopropyl-7-[(1R*,5S*)-6-hydroxy-3-azabicyclo[3,3,0]octane-3-yl]-6,8-difluoro-1,4-dihydro-4-oxo-3-quinolinecarboxylic acid (I-44)

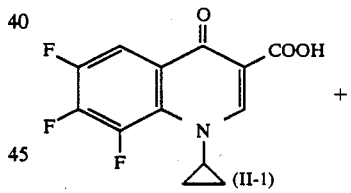

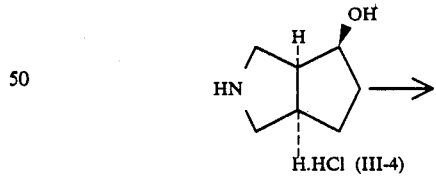

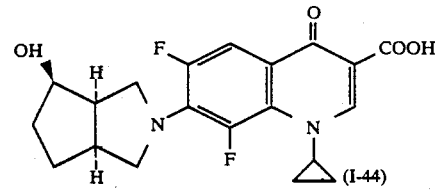

The reaction is performed as described in Example 43, whereby the objective compound (I-44) 150 mg (Yield: 64%) is obtained.

Anal Calcd. (%) for C₂₀H₂₀F₂N₂O₄: C, 61.53; H, 5.16; F, 9.03; N, 7.18 Found (%): C, 61.52; H, 5.16; F, 9.51; N, 7.22

EFFECT OF THE INVENTION

Experiment (Antibacterial spectrum)

The antibacterial activity was determined by measuring minimum growth inhibitory concentrations in accordance with the method designated by the Japan Society of Chemotherapy. The results are shown in Table 3.

A, B, C and D in the table indicate the following meanings:

A: Staphylococcus aureus SMITH
B: Staphylococcus aureus SR77
C: Escherichia coli EC-14
D: Escherichia coli SR377 (R)

The test microorganisms were used at $10^6$ cells/ml.

TABLE 5

| Compound No. | Minimum Inhibitory Concentrations (μg/ml) | | | |
|---|---|---|---|---|
| | A | B | C | D |
| I-4 | ≦0.006 | 0.025 | 0.05 | 0.39 |
| I-22 | 0.025 | 0.1 | 0.1 | 0.2 |
| I-23 | ≦0.006 | 0.025 | 0.05 | 0.2 |
| I-24 | ≦0.006 | 0.0125 | 0.05 | 0.1 |
| I-27 | 0.025 | 0.2 | 0.05 | 0.2 |
| I-28 | 0.025 | 0.1 | 0.1 | 0.39 |
| I-29 | 0.0125 | 0.025 | 0.1 | 0.2 |
| I-30 | 0.0125 | 0.05 | 0.05 | 0.2 |
| I-44 | 0.0125 | 0.05 | 0.05 | — |
| OFL | 0.39 | 0.78 | 0.1 | 0.1 |

OFL: ofloxacin (Reference drug)

These results have clarified that compounds of this invention show strong antibacterial activities particularly against gram-positive bacteria.

What we claim is:

1. A compound of the formula:

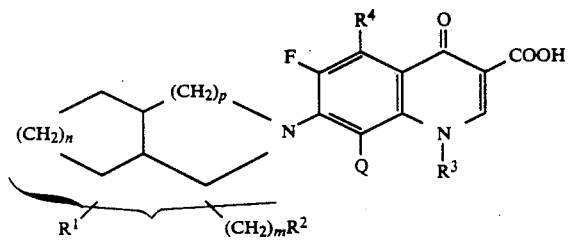

wherein $R^1$ is hydrogen, hydroxy, $C_1$–$C_4$ alkyl, oxo, or amino; $R^2$ is hydrogen, hydroxy, or amino optionally substituted by $C_1$–$C_4$ alkyl; $R^3$ is $C_1$–$C_4$ alkyl, $C_3$–$C_5$ cycloalkyl, or mono or di-fluorophenyl; $R^4$ is hydrogen, hydroxy, or amino; Q is halogen; m is an integer of 0 or 1; n is an integer of 1, 2, or 3; p is an integer of 1 or 2, or a pharmaceutically acceptable salt thereof.

2. An antibacterial composition comprising an antibacterially effective amount of a compound claimed in claim 1 as an active ingredient and a pharmaceutically acceptable carrier therefor.

3. A compound claimed in claim 1 namely, 1-cyclopropyl-7-[(1R*, 5S*,6S*)-6-aminomethyl-3-azabicyclo[3,3,0]octane-3-yl]-6,8-difluoro-1,4-dihydro-4-oxo-3-quinolinecarboxylic acid.

4. A compound claimed in claim 1, namely, 1-cyclopropyl-7-[(1R*, 5S*,6R*)-6-amino-5-hydroxy-3-azabicyclo[3,3,0]octane-3-yl]-6,8-difluoro-1,4-dihydro-4-oxo-3-quinolinecarboxylic acid.

5. A compound claimed in claim 1, namely, 1-cyclopropyl-7-[(1R*, 5R*,6S*)-6-amino-5-hydroxy-3-azabicyclo[3,3,0]octane-3-yl]-6,8-difluoro-1,4-dihydro-4-oxo-3-quinolinecarboxylic acid.

6. A compound claimed in claim 1, namely, 1-cyclopropyl-7-[(1R*, 2R*,6S*)-2-amino-8-azabicyclo[4,3,0]nonane-8-yl]-5-amino-6,8-difluoro-1,4-dihydro-4-oxo-3-quinolinecarboxylic acid.

7. A compound claimed in claim 1, namely, 1-cyclopropyl-7-[(1R*, 6R*,7S*)-7-amino-3-azabicyclo[4,4,0]decane-3-yl]-6,8-difluoro-1,4-dihydro-4-oxo-3-quinolinecarboxylic acid.

8. A compound claimed in claim 1, namely, 1-cyclopropyl-7-[(1R*, 2S*,6S*)-2-amino-8-azabicyclo[4,3,0]nonane-8-yl]-5-amino-6,8-difluoro-1,4-dihydro-4-oxo-3-quinolinecarboxylic acid.

9. A compound claimed in claim 1, namely, 1-cyclopropyl-7-[(1R*, 5S*)-5-methylaminomethyl-3-azabicyclo[3,3,0]octane-3-yl]-5-amino-6,8-difluoro-1,4-dihydro-4-oxo-3-quinolinecarboxylic acid.

10. A compound claimed in claim 1, namely, 1-cyclopropyl-7-[(1R*,5S*,6S*)-6-amino-3-azabicyclo[3,3,0]octane-3-yl]-5-amino-6,8-difluoro-1,4-dihydro-4-oxo-3-quinolinecarboxylic acid.

11. A compound claimed in claim 1, namely, 1-cyclopropyl-7-[(1R*,6R*,10R*)-10-amino-3-azabicyclo[4,4,0]decane-3-yl]-6,8-difluoro-1,4-dihydro-4-oxo-3-quinolinecarboxylic acid.

12. A compound claimed in claim 1, namely, 1-cyclopropyl-7-[(1R*,5S*,7S*)-7-amino-3-azabicyclo[3,3,0]octane-3-yl]-6,8-difluoro-1,4-dihydro-4-oxo-3-quinolinecarboxylic acid.

13. A compound claimed in claim 1, namely, 1-cyclopropyl-7-[(1R*,5S*)-1-methylaminomethyl-3-azabicyclo[3,3,0]octane-3-yl]-5-hydroxy-6,8-difluoro-1,4-dihydro-4-oxo-3-quinolinecarboxylic acid.

14. A compound claimed in claim 1, namely, 1-cyclopropyl-7-[(1R*,6S*,7S*)-7-amino-3-azabicyclo[4,3,0]nonane-3-yl]-6,8-difluoro-1,4-dihydro-4-oxo-3-quinolinecarboxylic acid.

15. A compound claimed in claim 1, namely, 1-cyclopropyl-7-[(1R*,6R*,9S*)-9-amino-3-azabicyclo[4,3,0]nonane-3-yl]-6,8-difluoro-1,4-dihydro-4-oxo-3-quinolinecarboxylic acid.

16. A compound claimed in claim 1, namely, 1-cyclopropyl-7-[(1R*,2S*,6S*)-2-amino-7-azabicyclo[4,3,0]nonane-7-yl]-6,8-difluoro-1,4-dihydro-4-oxo-3-quinolinecarboxylic acid.

17. A compound claimed in claim 1, namely, 1-cyclopropyl-7-[(1R*,2R*,7S*)-2-amino-9-azabicyclo[5,3,0]decane-9-yl]-5-amino-6,8-difluoro-1,4-dihydro-4-oxo-3-quinolinecarboxylic acid.

18. A compound claimed in claim 1, namely, 1-(2,4-difluorophenyl)-7-[(1R*,5S*)-1-aminomethyl-3-azabicyclo[3,3,0]octane-3-yl]-6,8-difluoro-1,4-dihydro-4-oxo-3-quinolinecarboxylic acid.

19. A compound claimed in claim 1, namely, 1-cyclopropyl-7-[(1R*,5S*,6S*)-6-amino-3-azabicyclo[3,3,0]octane-3-yl]-6,8-difluoro-1,4-dihydro-4-oxo-3-quinolinecarboxylic acid.

20. A compound claimed in claim 1, namely, 1-cyclopropyl-7-[(1R*,5S*)-1-aminomethyl-3-azabicyclo[3,3,0]octane-3-yl]-6,8-difluoro-1,4-dihydro-4-oxo-3-quinolinecarboxylic acid.

21. A compound claimed in claim 1, namely, 1-cyclopropyl-7-[(1R*,5S*)-1-amino-3-azabicyclo[3,3,0]octane-3-yl]-6,8-difluoro-1,4-dihydro-4-oxo-3-quinolinecarboxylic acid.

22. A compound claimed in claim 1, namely, 1-cyclopropyl-7-[(1R*,5S*,6S*)-6-methylamino-3-azabicyclo[3,3,0]octane-3-yl]-6,8-difluoro-1,4-dihydro-4-oxo-3-quinolinecarboxylic acid.

23. A compound claimed in claim 1, namely, 1-cyclopropyl-7-[(1R*,2R*,6S*)-2-methyl-8-azabicyclo[4,3,0]nonane-8-yl]-6,8-difluoro-1,4-dihydro-4-oxo-3-quinolinecarboxylic acid.

24. A compound claimed in claim 1, namely, 1-cyclopropyl-7-[(1R*,5S*,6R*)-6-amino-3-azabicyclo[3,3,0]octane-3-yl]-6,8-difluoro-1,4-dihydro-4-oxo-3-quinolinecarboxylic acid.

25. A compound claimed in claim 1, namely, 1-cyclopropyl-7-[(1R*,2R*,6S*)-2-amino-8-azabicyclo[4,3,0]nonane-8-yl]-8-chloro-6-fluoro-1,4-dihydro-4-oxo-3-quinolinecarboxylic acid.

26. A compound claimed in claim 1, namely, 1-cyclopropyl-7-[(1R*,2S*,6S*)-2-amino-8-azabicyclo[4,3,0]nonane-8-yl]-6,8-difluoro-1,4-dihydro-4-oxo-3-quinolinecarboxylic acid.

27. A compound claimed in claim 1, namely, 1-cyclopropyl-7-[(1R*,2R*,6S*)-2-methylamino-8-azabicyclo[4,3,0]nonane-8-yl]-6,8-difluoro-1,4-dihydro-4-oxo-3-quinolinecarboxylic acid.

28. A compound claimed in claim 1, namely, 1-cyclopropyl-7-[(1R*,2R*,7S*)-2-amino-9-azabicyclo[5,3,0]decane-9-yl]-6,8-difluoro-1,4-dihydro-4-oxo-3-quinolinecarboxylic acid.

29. A compound claimed in claim 1, namely, 1-cyclopropyl-7-[(1R*,5S*,7S*)-7-amino-3-azabicyclo[3,3,0]octane-3-yl]-6,8-difluoro-1,4-dihydro-4-oxo-3-quinolinecarboxylic acid.

30. A compound claimed in claim 1, namely, 1-cyclopropyl-7-[(1R*,5S*)-1-methylaminomethyl-3-azabicyclo[3,3,0]octane-3-yl]-6,8-difluoro-1,4-dihydro-4-oxo-3-quinolinecarboxylic acid.

31. A compound claimed in claim 1, namely, 1-cyclopropyl-7-[(1R*,5S*)-1-ethylaminomethyl-3-azabicyclo[3,3,0]octane-3-yl]-6,8-difluoro-1,4-dihydro-4-oxo-3-quinolinecarboxylic acid.

32. A compound claimed in claim 1, namely, 1-cyclopropyl-7-[(1R*,6S*)-1-methylaminomethyl-8-azabicyclo[4,3,0]nonane-8-yl]-6,8-difluoro-1,4-dihydro-4-oxo-3-quinolinecarboxylic acid.

33. A compound claimed in claim 1, namely, 1-ethyl-7-[(1R*,5S*, 6R*)-6-amino-3-azabicyclo[3,3,0]octane-3-yl]-6,8-difluoro-1,4-dihydro-4-oxo-3-quinolinecarboxylic acid.

34. A compound claimed in claim 1, namely, 1-cyclopropyl-7-[(1R*,2S*,7S*)-2-methylamino-9-azabicyclo[5,3,0]decane-9-yl]-6,8-difluoro-1,4-dihydro-4-oxo-3-quinolinecarboxylic acid.

35. A compound claimed in claim 1, namely, 1-cyclopropyl-7-[(1R*,2S*,7S*)-2-amino-9-azabicyclo[5,3,0]decane-9-yl]-6,8-difluoro-1,4-dihydro-4-oxo-3-quinolinecarboxylic acid.

36. A compound claimed in claim 1, namely, 1-cyclopropyl-7-[(1R*,2R*,7S*)-2-methylamino-9-azabicyclo[5,3,0]decane-9-yl]-6,8-difluoro-1,4-dihydro-4-oxo-3-quinolinecarboxylic acid.

37. A compound claimed in claim 1, namely, 1-cyclopropyl-7-[(1R*,2S*,7S*)-2-methylamino-9-azabicyclo[5,3,0]decane-9-yl]-6,8-difluoro-1,4-dihydro-4-oxo-3-quinolinecarboxylic acid.

38. A compound claimed in claim 1, namely, 1-cyclopropyl-7-[(1R*,5S*)-6-oxo-3-azabicyclo[3,3,0]octane-3-yl]-6,8-difluoro-1,4-dihydro-4-oxo-3-quinolinecarboxylic acid.

39. A compound claimed in claim 1, namely, 1-cyclopropyl-7-[(1R*,5S*)-6-hydroxy-3-azabicyclo[3,3,0]octane-3-yl]-6,8-difluoro-1,4-dihydro-4-oxo-3-quinolinecarboxylic acid.

* * * * *